United States Patent
Mahadeshwar et al.

(10) Patent No.: US 7,163,675 B2
(45) Date of Patent: Jan. 16, 2007

(54) SHAMPOO COMPOSITIONS

(75) Inventors: Anand Ramchandra Mahadeshwar, Merseyside (GB); Ruby Loo Bick Tan-Walker, Merseyside (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 741 days.

(21) Appl. No.: 10/312,980

(22) Filed: Jan. 3, 2003

(65) Prior Publication Data

US 2004/0101502 A1    May 27, 2004

(30) Foreign Application Priority Data

Jul. 7, 2000    (GB) ................... 0016807.0

(51) Int. Cl.
*A61Q 5/02* (2006.01)

(52) U.S. Cl. ............... 424/70.19; 424/70.28; 424/70.12; 424/70.22

(58) Field of Classification Search ............ None
See application file for complete search history.

(56) References Cited

U.S. PATENT DOCUMENTS

| 4,529,586 A | 7/1985 | De Marco et al. |
| 4,710,314 A | 12/1987 | Madrange et al. |
| 5,151,210 A | 9/1992 | Steuri et al. |
| 5,747,436 A | 5/1998 | Patel et al. |
| 5,756,076 A | 5/1998 | Cervantes et al. |
| 6,274,130 B1 * | 8/2001 | Murray .................. 424/70.12 |

FOREIGN PATENT DOCUMENTS

| GB | 2177108 A | 1/1987 |
| JP | 06/293620 A | 6/1994 |
| WO | 98/19655 | 5/1998 |
| WO | 98/19656 | 5/1998 |
| WO | 99/15134 | 4/1999 |
| WO | 66/29286 | 6/1999 |
| WO | 99/29286 | 6/1999 |
| WO | 99/44565 | 9/1999 |

OTHER PUBLICATIONS

International Search Report Application No. PCT/EP 01/07171 mailed Dec. 12, 2001.
JP 09/052,820 A to Fujiwara (Jun. 1997) assigned to Mandamu:KK (Patent Abstract of Japan, vol. 1997, No. 06).

* cited by examiner

*Primary Examiner*—Jyothsna Venkat
(74) *Attorney, Agent, or Firm*—Karen E. Klumas

(57) ABSTRACT

This invention provides aqueous shampoo compositions comprising, in addition to water, an anionic surfactant, a cationic surfactant, and emulsified cationic particles of silicone.

5 Claims, No Drawings

SHAMPOO COMPOSITIONS

FIELD OF THE INVENTION

This invention relates to hair shampoo compositions which contain a combination of anionic surfactant, cationic surfactant and emulsified cationic particles of silicone. The compositions provide conditioning benefits, enhanced removal of oily materials accumulated on the hair, and superior clean feel, especially amongst consumers who oil their hair.

BACKGROUND AND PRIOR ART

Conditioning hair treatments comprising various combinations of cleansing surfactant and hair conditioning agents are known. These shampoo products typically comprise an anionic surfactant in combination with a conditioning agent such as silicone. The silicone is deposited onto the hair resulting in the formation of a film. The silicone film gives excellent conditioning but a problem is that it may also result in a heavy, oily feel, particularly amongst consumers who oil in their hair. The oiling habit is widely practised by around 800 million people across the Central Asia and Middle East region. Pre wash oiling is done as it is believed that oils nourish hair and protect it during the wash process. Post wash oiling is done for manageability and styling.

There is therefore a need for a shampoo which can provide conditioning benefits to the hair without adversely affecting its clean feel.

The present inventors have found that shampoo compositions which contain a combination of anionic surfactant, cationic surfactant and emulsified cationic particles of silicone provide conditioning benefits, enhanced removal of oily materials accumulated on the hair, and superior clean feel, especially amongst consumers who oil their hair.

WO 99/29286 provides hair treatment compositions for superior conditioning which comprise a combination of amino functionalised silicone and hydroxyl functionalised silicone. The compositions may be formulated as a shampoo with anionic surfactant or as a conditioner with cationic surfactant.

U.S. Pat. No. 5,756,076 describes a cleansing and conditioning composition for the hair based on an alkylpolyglycoside-type surfactant washing base combined with a conditioner system comprising fatty alcohol, cationic surfactant and optional cationic silicone.

U.S. Pat. No. 4,529,586 describes a conditioner for application to hair before or after shampooing which incorporates a cationic emulsion of an amino-functional silicone polymer in combination with a cationic surfactant-emulsifier and a cationic polymer. This is said to improved deposition of the silicone on the hydrophilic hair surface.

GB 2,177,108 and U.S. Pat. No. 5,151,210 describe shampoos comprising anionic surfactant, suspending agent, a lauryl trimethyl quaternary ammonium salt and a silicone which may be a polyalkyl siloxane, a polyaryl siloxane, a polyalkylaryl siloxane or a polyether siloxane copolymer. The shampoos are said to possess good stability and provide superior hair conditioning.

JP 06/293,620 describes a shampoo containing a lauryl trimethyl quaternary ammonium salt in conjunction with anionic and amphoteric surfactant. The shampoo is said to show good foamability and softening properties without damaging the hair.

U.S. Pat. No. 5,747,436 describes a conditioning shampoo which exhibits enhanced antistatic properties due to the use of a specific mixture of monoalkyl quaternary ammonium salt and di-alkyl ethoxylated quaternary salt. The advantage of this is said to be that effective, low cost conditioning shampoos can be prepared which are free of conditioning amounts of silicone conditioning agents.

None of the above documents disclose or suggest a combination of anionic surfactant, cationic surfactant and emulsified cationic particles of silicone in a shampoo to provide enhanced conditioning, oil removal and clean feel.

SUMMARY OF THE INVENTION

The present invention provides an aqueous shampoo composition comprising, in addition to water:
i) an anionic surfactant;
ii) a cationic surfactant, and
iii) emulsified cationic particles of silicone.

DETAILED DESCRIPTION AND PREFERRED EMBODIMENTS

Anionic Surfactant

Shampoo compositions according to the invention comprise one or more anionic surfactants which are cosmetically acceptable and suitable for topical application to the hair.

Examples of suitable anionic surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic surfactants for use in shampoos of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n ranges from 1 to 3), ammonium lauryl sulphate and ammonium lauryl ether sulphate(n)EO, (where n ranges from 1 to 3).

Mixtures of any of the foregoing anionic surfactants may also be suitable.

The total amount of anionic surfactant in shampoo compositions of the invention (including any which may be present as emulsifier for hydrophobic ingredients of the shampoo composition) is generally from 5 to 30%, preferably from 6 to 20%, more preferably from 8% to 16% by weight based on total weight of the shampoo composition.

Cationic Surfactant

Shampoo compositions according to the invention comprise one or more cationic surfactants which are cosmetically acceptable and suitable for topical application to the hair.

Cationic surfactants useful in compositions of the invention contain amino or quaternary ammonium hydrophilic moieties which are positively charged when dissolved in the aqueous composition of the present invention.

Examples of suitable cationic surfactants are those corresponding to the general formula:

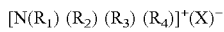

in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for shampoo compositions of the present invention are monoalkyl quaternary ammonium compounds in which the alkyl chain length is C8 to C14.

Suitable examples of such materials correspond to the general formula:

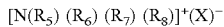

in which $R_5$ is a hydrocarbyl chain having 8 to 14 carbon atoms or a functionalised hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate, and alkylsulphate radicals.

The functionalised hydrocarbyl chains (b) may suitably contain one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof.

Preferably the hydrocarbyl chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of C8 to C12 hydrocarbyl chains.

Typical monoalkyl quaternary ammonium compounds of the above general formula for use in shampoo compositions of the invention include:
(i) lauryl trimethylammonium chloride(available commercially as Arquad C35 ex-Akzo); cocodimethyl benzyl ammonium chloride (available commercially as Arquad DMCB-80 ex-Akzo)
(ii) compounds of the general formula:

[N(R$_1$) (R$_2$) ((CH$_2$ CH$_2$ O)$_x$ H) ((CH$_2$CH$_2$O)$_y$H)]$^+$ (X)$^-$ in which:
x+y is an integer from 2 to 20;
$R_1$ is a hydrocarbyl chain having 8 to 14, preferably 12 to 14, most preferably 12 carbon atoms or a functionalised hydrocarbyl chain with 8 to 14, preferably 12 to 14, most preferably 12 carbon atoms and containing ether, ester, amido or amino moieties present as substituents or as linkages in the radical chain;
$R_2$ is a $C_1$–$C_3$ alkyl group or benzyl group, preferably methyl, and
X is a salt-forming anion such as those selected from halocen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB/12 ex-Akzo Nobel); PEG-5 cocomonium methosulphate (available commercially as Rewoquat CPEM ex-Rewo); PEG-15 cocomonium chloride (available commercially as Ethoquad C/25 ex-Akzo).

(iii) compounds of the general formula:

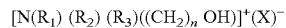

in which:
n is an integer from 1 to 4, preferably 2;
$R_1$ is a hydrocarbyl chain having 8 to 14, preferably 12 to 14, most preferably 12 carbon atoms;
$R_2$ and $R_3$ are independently selected from $C_1$–$C_3$ alkyl groups, and are preferably methyl, and
X is a salt-forming anion such as those selected from halogen, (e.g. chloride, bromide), acetate, citrate, lactate, glycolate, phosphate nitrate, sulphate, and alkylsulphate radicals.

Suitable examples are lauryldimethylhydroxyethylammonium chloride (available commercially as Prapagen HY ex-Clariant).

Mixtures of any of the foregoing cationic surfactants compounds may also be suitable.

The total amount of cationic surfactant in shampoo compositions of the invention (including any which may be present as emulsifier for hydrophobic ingredients of the shampoo composition) is generally from 0.05 to 10%, preferably from 0.1 to 7.5%, more preferably from 0.25% to 5% by weight based on total weight of the shampoo composition.

Emulsified Cationic Particles of Silicone

Shampoo compositions of the invention comprise emulsified cationic particles of silicone.

As used herein, the term "emulsified cationic particles of silicone" means (a): materials in which the positive charge providing the cationic character is located on the silicone particles themselves; as well as (b): materials in which the silicone particles, irrespective of their own charge, have been emulsified with a cationic emulsifier prior to their incorporation into the shampoo composition.

Suitably the silicone particles in shampoo compositions of the invention will have an average silicone particle size in the shampoo composition of less than 30, preferably less than 20, more preferably less than 10 microns. Most preferably the average silicone particle size in the shampoo composition is less than 2 microns, ideally it ranges from 0.01 to 0.5 micron. Silicone emulsions having an average silicone particle size of ≦0.15 microns are generally termed microemulsions.

Particle size may be measured by means of a laser light scattering technique, using a 2600D Particle Sizer from Malvern Instruments.

Suitable examples of materials in which the positive charge providing the cationic character is located on the silicone particles themselves include amino functionalised silicones.

By "amino functionalised silicone" is meant a silicone containing at least one primary, secondary or tertiary amine group, or a quaternary ammonium group.

Examples include:

(i) polysiloxanes having the CTFA designation "amodimethicone", and the general formula:

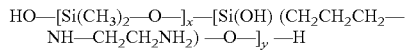

in which x and y are numbers depending on the molecular weight of the polymer, generally such that the molecular weight is between about 5,000 and 500,000.

(ii) polysiloxanes having the general formula:

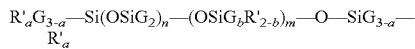

in which:

G is selected from H, phenyl, OH or $C_{1-8}$ alkyl, e.g. methyl;

a is 0 or an integer from 1 to 3, preferably 0;

b is 0 or 1, preferably 1;

m and n are numbers such that (m+n) can range from 1 to 2000, preferably from 50 to 150;

m is a number from 1 to 2000, preferably from 1 to 10;

n is a number from 0 to 1999, preferably from 49 to 149, and

R' is a monovalent radical of formula —$C_qH_{2q}$L in which q is a number from 2 to 8 and L is an amino functional group selected from the following:

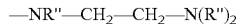

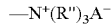

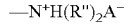

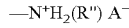

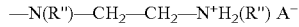

in which R" is selected from H, phenyl, benzyl, or a saturated monovalent hydrocarbon radical, e.g. $C_{1-20}$ alkyl, and A is a halide ion, e.g. chloride or bromide.

Suitable amino functionalised silicones corresponding to the above formula include those polysiloxanes termed "trimethylsilylamodimethicone" as depicted below, and which are sufficiently water insoluble so as to be useful in shampoo compositions of the invention:

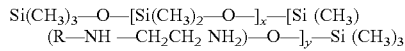

wherein x+y is a number from about 50 to about 500, and wherein R is an alkylene group having from 2 to 5 carbon atoms. Preferably, the number x+y is in the range of from about 100 to about 300.

(iii) quaternary silicone polymers having the general formula:

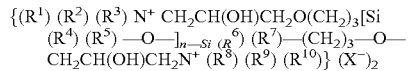

wherein $R^1$ and $R^{10}$ may be the same or different and may be independently selected from H, saturated or unsaturated long or short chain alk(en)yl, branched chain alk(en)yl and $C_5$-$C_8$ cyclic ring systems;

$R^2$ thru' $R^9$ may be the same or different and may be independently selected from H, straight or branched chain lower alk(en)yl, and $C_5$-$C_8$ cyclic ring systems;

n is a number within the range of about 60 to about 120, preferably about 80, and $X^-$ is preferably acetate, but may instead be for example halide, organic carboxylate, organic sulphonate or the like.

Suitable quaternary silicone polymers of this class are described in EP-A-0 530 974.

Amino functionalised silicones suitable for use in shampoo compositions of the invention will typically have a mole % amine functionality in the range of from about 0.1 to about 8.0 mole %, preferably from about 0.1 to about 5.0 mole %, most preferably from about 0.1 to about 2.0 mole %. In general the amine concentration should not exceed about 8.0 mole %.

The viscosity of the amino functionalised can suitably range from about 100 to about 500,000 cst.

Specific examples of amino functionalised silicones suitable for use in shampoo compositions of the invention are the aminosilicone oils DC2-8220, DC2-8055, DC2-8162, and DC2-8950-114 (all ex Dow Corning), and GE 1149-75, (ex General Electric Silicones).

Also suitable are pre-formed emulsions of amino functionalised silicones with non ionic and/or cationic emulsifier.

Pre-formed emulsions of amino functionalised silicones are available from suppliers of silicone oils such as Dow Corning and General Electric. Specific examples include DC929 Cationic Emulsion, DC939 Cationic Emulsion, DC949 Cationic Emulsion, and the emulsions DC2-7224 and DC2-8154 (all ex Dow Corning).

An example of a quaternary silicone polymer useful in the present invention is the material K3474, ex Goldschmidt.

As described above, also suitable for use in shampoo composition of the invention are materials in which the silicone particles, irrespective of their own charge, have been emulsified with a cationic emulsifier prior to their incorporation into the shampoo composition.

Examples of such materials include pre-formed emulsions of nonionic silicones (such as polydimethylsiloxanes having the CTFA designation "dimethicone" and/or hydroxyl functionalised polydimethylsiloxanes having the CTFA designation "dimethiconol") with cationic surfactant (such as cetyltrimethylammonium chloride and/or tallowtrimethylammonium chloride). A suitable commercially available example is emulsion DC1669 ex Dow Corning.

Mixtures of any of the foregoing types of silicones may also be suitable.

The total amount of emulsified cationic particles of silicone in shampoo compositions of the invention is generally from 0.01 to 10%, preferably from 0.05 to 7.5%, more preferably from 0.1% to 5% by weight based on total weight of the shampoo composition.

Clearly, the present invention does not encompass shampoo compositions in which the only cationic surfactant present is that derived from cationic surfactant used as an emulsifier in pre-formed emulsions of cationic particles of silicone. Where cationic surfactant derived from a pre-emulsion is present, additional cationic surfactant must also be included in the compositions of the invention to achieve the benefit of the invention. Furthermore, where cationic surfactant derived from a pre-emulsion is present, the "additional" cationic surfactant preferably amounts to at least 50 wt. %, more preferably at least 75 wt. %, and yet more preferably at least 90 wt. % of the total cationic surfactant present.

Optional Ingredients

A cationic polymer is a preferred optional ingredient in shampoo compositions of the invention. By "cationic polymer" is meant a polymer having cationic nitrogen containing groups such as quaternary ammonium or protonated amino groups, or a mixture thereof, which does not contain silicon atoms.

The cationic polymer may be a homopolymer or be formed from two or more types of monomers. The molecular weight of the polymer will generally be between 5 000 and 10 000 000, typically at least 10 000 and preferably in the range 100 000 to about 2 000 000.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range. Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerised in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:
copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);
copolymers of 1-vinyl-2-pyrrolidine and dimethylaminoethyl methacrylate, referred to in the industry (CTFA) as Polyquaternium-11. This material is available commercially from GAF Corporation (Wayne, N.J., USA) under the GAFQUAT tradename (e.g., GAFQUAT 755N);
cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo-and co-polymers of unsaturated carboxylic acids having from 3 to 5 carbon atoms, (as described in U.S. Pat. No. 4,009,256);
cationic polyacrylamides (as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use in compositions of the invention include those of the formula:

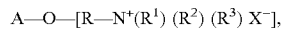

$$A-O-[R-N^+(R^1)(R^2)(R^3)X^-],$$

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (Commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17, having a high degree of substitution and a high viscosity, JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic polymer is selected from cationic cellulose and cationic guar gum derivatives.

Mixtures of any of the foregoing cationic polymers may also be suitable.

The cationic polymer may be present in an amount generally ranging from about 0.01 to about 5% by weight of the total shampoo composition, preferably from 0.01 to 1% by weight.

A particularly preferred level of cationic polymer in compositions of the invention ranges from 0.05 to 0.25% by weight, since this delivers excellent sensory properties.

The shampoo composition can optionally include co-surfactants, to help impart aesthetic, physical or cleansing properties to the composition.

A preferred example is an amphoteric or zwitterionic surfactant, which can be included in a total amount (including any which may be present as emulsifier for hydrophobic ingredients of the shampoo composition) ranging from 0 to about 8%, preferably from 1 to 4% by weight based on total weight of the shampoo composition.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred example is a nonionic surfactant, which can be included in a total amount (including any which may be present as emulsifier for hydrophobic ingredients of the shampoo co-position) ranging from 0% to about 8% preferably from 2 to 5% by weight based on total weight of the shampoo composition.

For example, representative nonionic surfactants that can be included in shampoo compositions of the invention include condensation products of aliphatic ($C_8$–$C_{18}$) primary or secondary, l;near or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

RO–(G)$_n$ wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in shampoo compositions of the invention include the $C_{10}$–$C_{18}$ N-alkyl ($C_1$–$C_6$) polyhydroxy fatty acid amides, such as the $C_{12}$–$C_{18}$ N-methyl glucamides, as described for example in WO 92 06154 and U.S. Pat. No. 5,194,639, and the N-alkoxy polyhydroxy fatty acid amides, such as $C_{10}$–$C_{18}$ N-(3-methoxypropyl) glucamide.

Other Optional Ingredients

Shampoo compositions of this invention may contain any other ingredient normally used in shampoo compositions. These other ingredients may include viscosity modifiers, preservatives, colouring agents, polyols such as glycerine and polypropylene glycol, chelating agents such as EDTA, antioxidants such as vitamin E acetate, fragrances, antimicrobials and sunscreens. Each of these ingredients will be present in an amount effective to accomplish its purpose. Generally these optional ingredients are included individually at a level of up to about 5% by weight of the total composition.

The invention is further illustrated by way of the following non-limitative Examples, in which all percentages quoted are by weight based on total weight unless otherwise stated.

EXAMPLES

Shampoo formulations were made up having ingredients as shown in the following Table. Comp. Ex. A and Comp. Ex. B are comparative examples. Ex.1 and Ex.2 are examples according to the invention.

| Ingredient | Control | Comp. Ex. A | Comp. Ex. B | Ex. 1 | Ex. 2 |
|---|---|---|---|---|---|
| Sodium laureth sulphate | 16 | 16 | 16 | 16 | 16 |
| Coco amidopropyl betaine | 2 | 2 | 2 | 2 | 2 |
| Jaguar C13S | 0.1 | 0.1 | 0.1 | 0.1 | 0.1 |
| Dimethicone emulsion | 2 | — | — | — | — |
| Cationic amodimethicone emulsion | — | 2 | — | — | — |
| Cationic dimethicone emulsion | — | — | 2 | 2 | 2 |
| Lauryl trimethyl ammonium chloride | — | — | — | 2 | 3 |
| Water | | | q. s. | | |

Test Method

Hair switches were oiled with a conmnercially-available blend of coconut oil and mineral oil. A fixed quantity of test formulation was applied onto the oiled hair switches, followed by washing and rinsing in accordance with normal procedures. On drying the switches were assessed by semi-trained panellists on a number of attributes and scored (0–100).

Evaluation Results

The rating scores are shown in the Tables below for the attributes described.

"Conditioning" is a measure of ease of comb and smooth feel.

"Clean/Shine" is a measure of clean feel, clean appearance, brightness and contrast.

Significance levels are indicated as follows:

TABLE 1

| Attribute | Comp. Ex. A | Control 1 | Level of significance |
|---|---|---|---|
| Conditioning | 77 | 55 | *** |
| Clean/Shine | 64 | 67 | |

\* $p < 0.05$
\*\* $p < 0.01$
\*\*\* $p < 0.001$

TABLE 2

| Attribute | Comp. Ex. B | Control | Level of significance |
|---|---|---|---|
| Conditioning | 84 | 55 | *** |
| Clean/Shine | 64 | 64 | |

TABLE 3

| Attribute | Ex. 1 | Control | Level of significance |
|---|---|---|---|
| Conditioning | 86 | 64 | *** |
| Clean/Shine | 73 | 66 | |

TABLE 4

| Attribute | Example 4 | Control | Level of significance |
|---|---|---|---|
| Conditioning | 73 | 63 | * |
| Clean/Shine | 66 | 40 | *** |

Conclusions

The results show that the examples according to the invention (Ex. 1 and Ex. 2) deliver improved results relative to the control on both conditioning and clean/shine. In contrast, the comparative examples (Comp. Ex. A and Comp. Ex. B) deliver improved conditioning relative to the control but no improvement in terms of clean/shine benefits.

What is claimed is:

1. An aqueous shampoo composition comprising, in addition to water:
    i) an anionic surfactant, wherein the total amount of anionic surfactant in the shampoo composition is from 5 to 30% by weight based on the total weight of the shampoo;
    ii) a cationic surfactant which is a monoalkyl quatemary ammonium compound in which the alkyl chain length is C8 to C14; and
    iii) emulsified cationic particles of silicone, in which the emulsified cationic particles of silicone are added to the shampoo composition as a pre-formed emulsion of amino functionalized silicone with nonionic and/or cationic surfactant, or in which the silicone particles, irrespective of their own charge, have been emulsified with a cationic emulsifier prior to their incorporation into the shampoo composition,
with the proviso that when cationic surfactant derived from the reformed emulsion is present, additional cationic surfactant is also included in the shampoo composition.

2. A shampoo composition according to claim 1, in which the anionic surfactant is selected from sodium lauryl sulphate, sodium lauryl ether sulphate(n)EO, (where n ranges from 1 to 3), ammonium lauryl sulphate and ammonium lauryl ether sulphate(n)EO, (where n ranges from 1 to 3), and mixtures thereof.

3. A composition according to claim 1, in which the emulsified cationic particles of silicone are added to the shampoo composition as a pre-formed emulsion of hydroxyl functionalised silicone with cationic surfactant.

4. A composition according to claim 1, in which the average silicone particle size in the shampoo composition is less than 2 microns.

5. A composition according to claim 1, which further comprises a cationic polymer selected from cationic cellulose, cationic guar gum derivatives, and mixtures thereof.

* * * * *